US00PP35672P2

(12) United States Plant Patent
Fleck et al.

(10) Patent No.: US PP35,672 P2
(45) Date of Patent: Mar. 5, 2024

(54) PLUM HYBRID ROOTSTOCK NAMED 'DA 6'

(50) Latin Name: ***Prunus* hybrid**
Varietal Denomination: DA 6

(71) Applicant: Sierra Gold Nurseries, Inc., Yuba City, CA (US)

(72) Inventors: Charles Edward Fleck, Yuba City, CA (US); Reid Robinson, Yuba City, CA (US)

(73) Assignee: Sierra Gold Nurseries, Inc., Yuba City, CA (US)

( * ) Notice: Subject to any disclaimer, the term of this patent is extended or adjusted under 35 U.S.C. 154(b) by 0 days.

(21) Appl. No.: 18/230,608

(22) Filed: Aug. 4, 2023

(51) Int. Cl.
*A01H 5/08* (2018.01)
*A01H 6/74* (2018.01)

(52) U.S. Cl.
USPC ..... Plt./184
CPC ..... *A01H 6/7472* (2018.05)

(58) Field of Classification Search
USPC ..... Plt./184
CPC ..... A01H 6/7472; A01H 5/08
See application file for complete search history.

*Primary Examiner* — Keith O. Robinson
(74) *Attorney, Agent, or Firm* — Michelle Bos Legal LLC

(57) ABSTRACT

A new and distinct hybrid plum tree named 'DA 6' developed for use as a rootstock and notable for the reduced vigor imparted to scions, good root strength, tolerance of wet soils and resistance to root-knot nematodes.

6 Drawing Sheets

Latin name: *Prunus* hybrid.
Variety denomination: 'DA 6'.

BACKGROUND OF THE VARIETY

'DA 6' is a new and distinct hybrid plum tree developed for use as a rootstock. 'DA 6' was selected from among seedlings obtained from the open pollination of *Prunus cerasifera* 'DRAM' Myrobalan plum seedlings (not patented) carried out at Yuba City, California in 2016. The 'DA 6' plum tree was selected for propagation and further observation in 2017. The first asexual propagation of the variety was carried out by hardwood cuttings at Yuba City, California in 2017. The variety has since been asexually reproduced through successive generations and has been observed to remain true to type.

BRIEF DESCRIPTION OF THE VARIETY

'DA 6' was selected because of the reduced vegetative vigor it imparts to grafted scions. 'DA 6' vigor is about 70% of the vigor of its female parent, and about 60% to 65% of standard rootstocks such as 'AP 1' (U.S. Plant Pat. No. 16,272, sold as Krymsk® 86). The root strength (tree anchorage) of 'DA 6' is notably higher than other vigor-reducing rootstocks such as 'HBOK 27' (U.S. Plant Pat. No. 23,631, sold as Controller 6) and 'Densipac' (U.S. Plant Pat. No. 23,865, sold as Rootpac®20). 'DA 6' is highly tolerant of wet soils, and exhibits improved almond scion graft compatibility as compared to the female parent. Minimal suckering and resistance to root-knot nematodes (*Meloidogyne* sp.) observed in 'DA 6' are similar to these traits observed in the female parent.

BRIEF DESCRIPTION OF THE PHOTOGRAPHS

The photographs were taken in 2023 at Yuba City, California. The tree shown is 6 years old.

Figure 1:
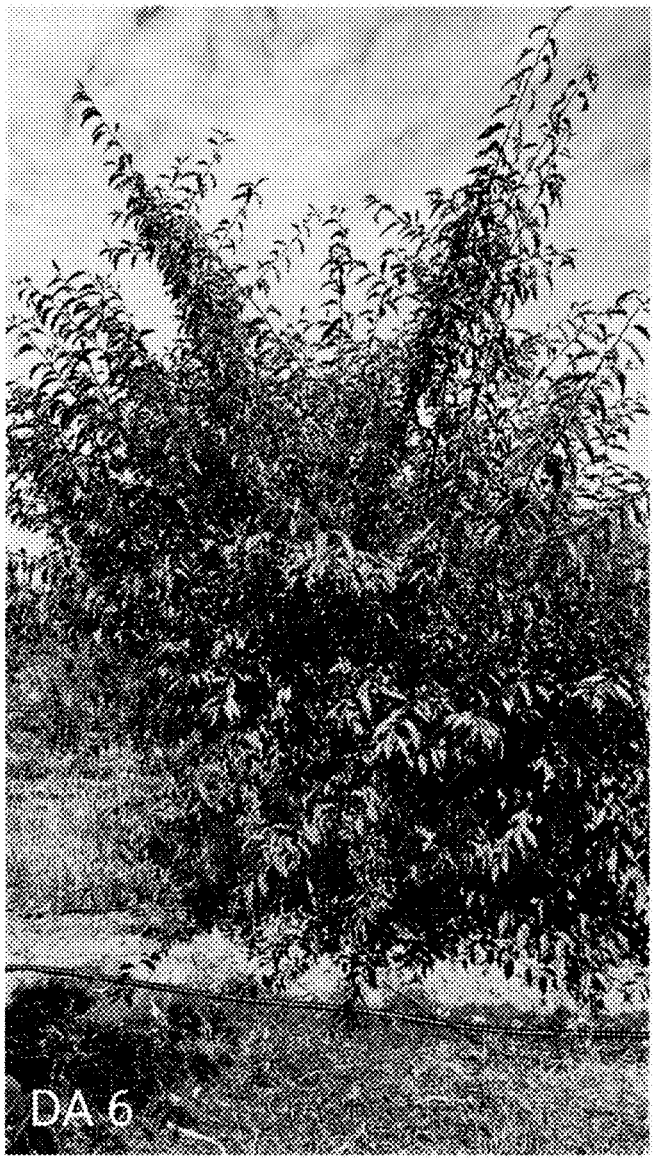
Figure 2:
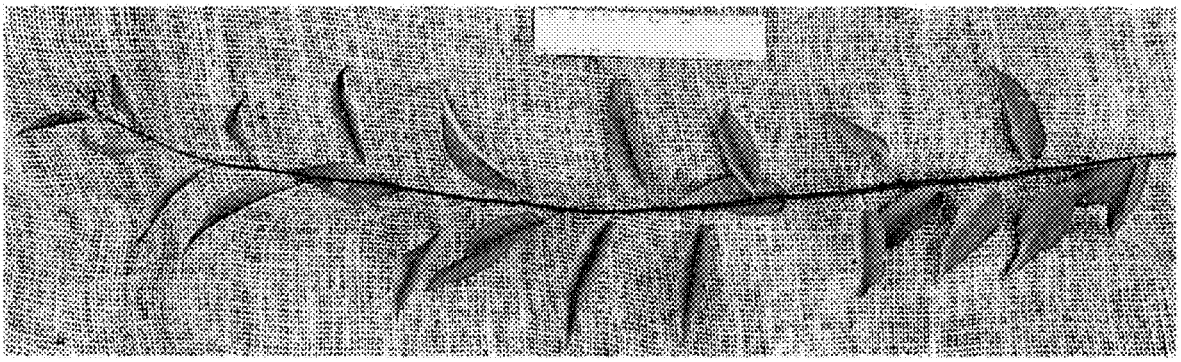
Figure 3:
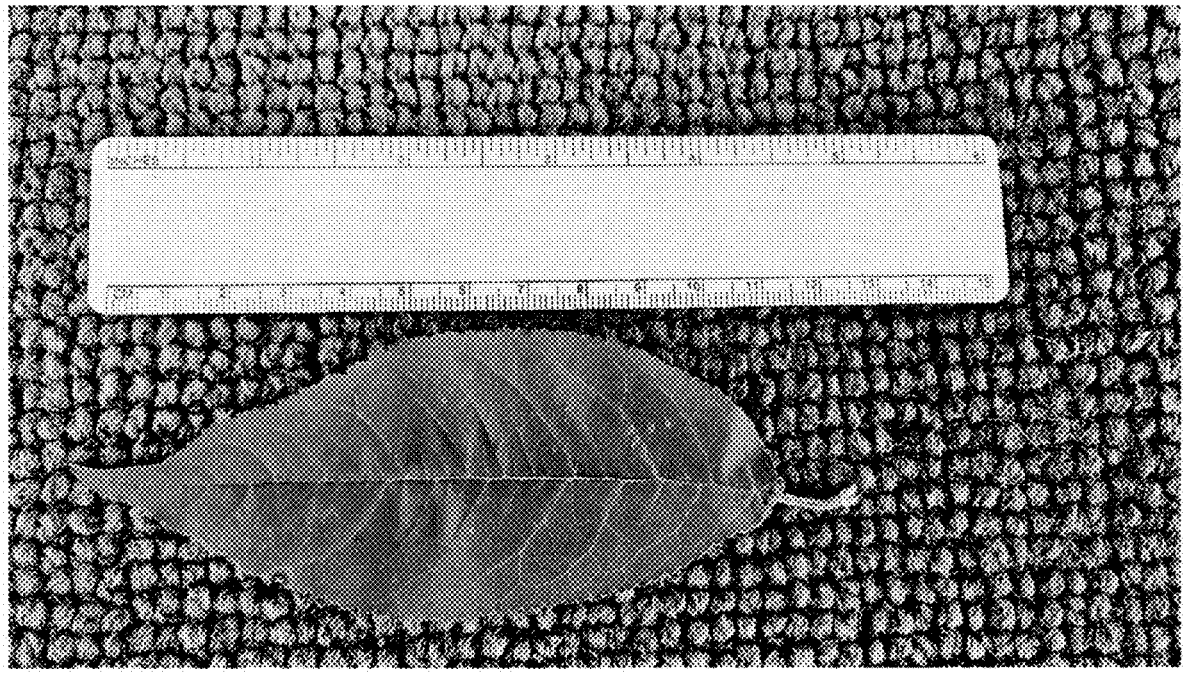
Figure 4:
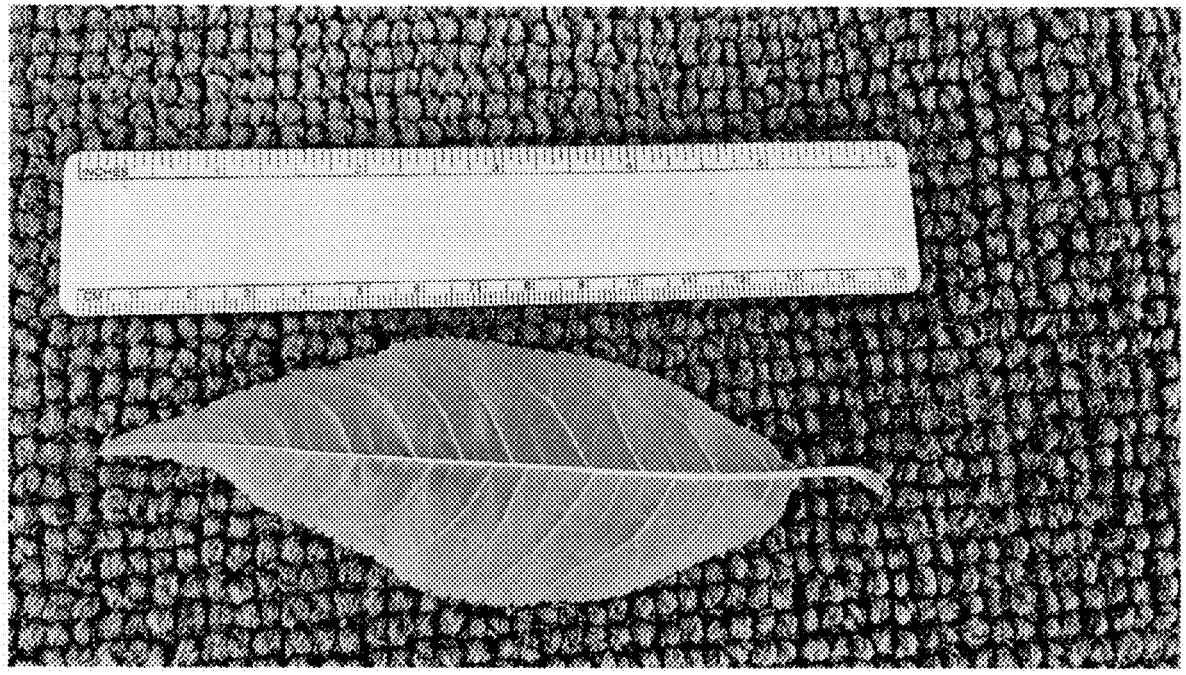
Figure 5:
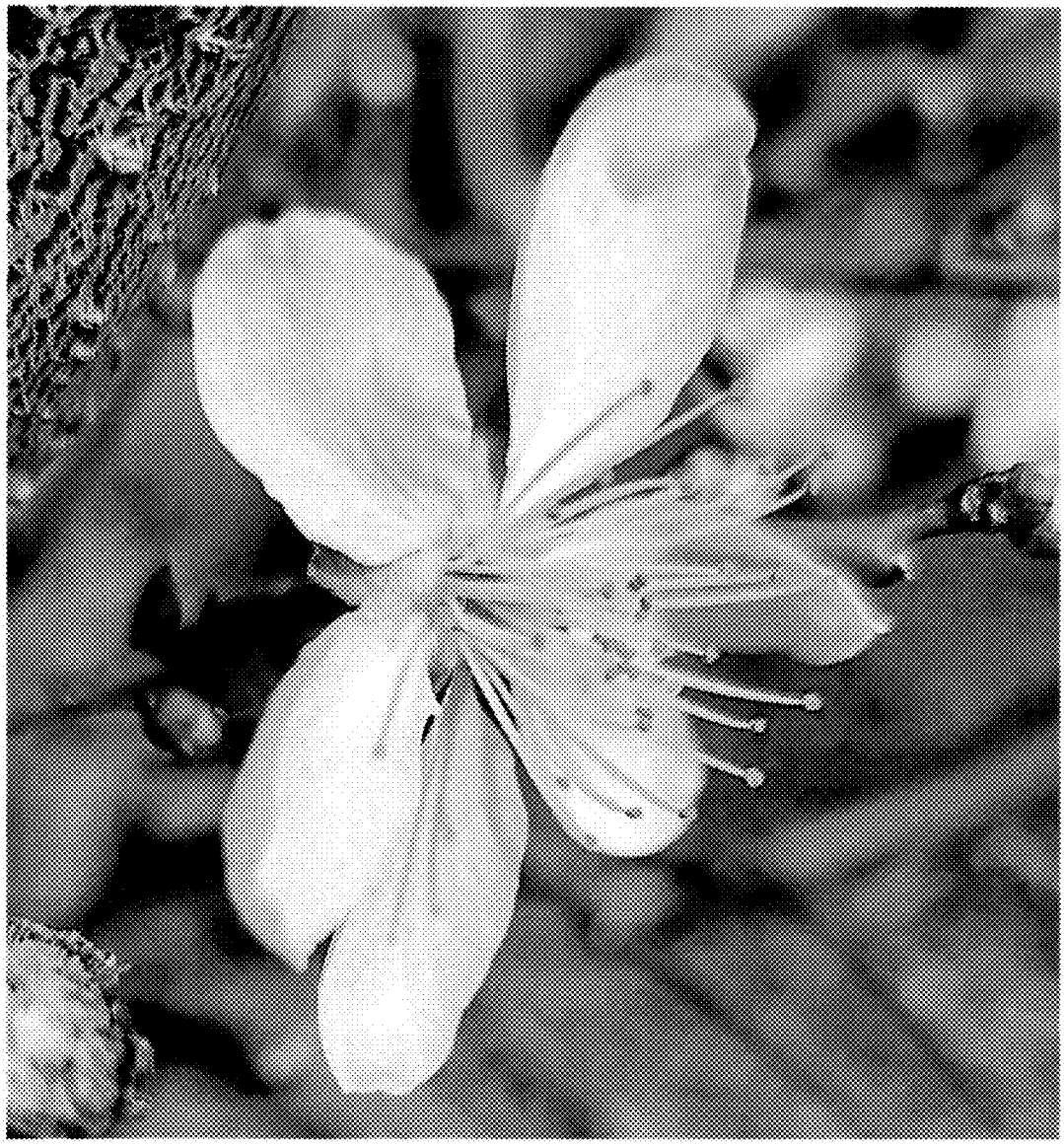
Figure 6:
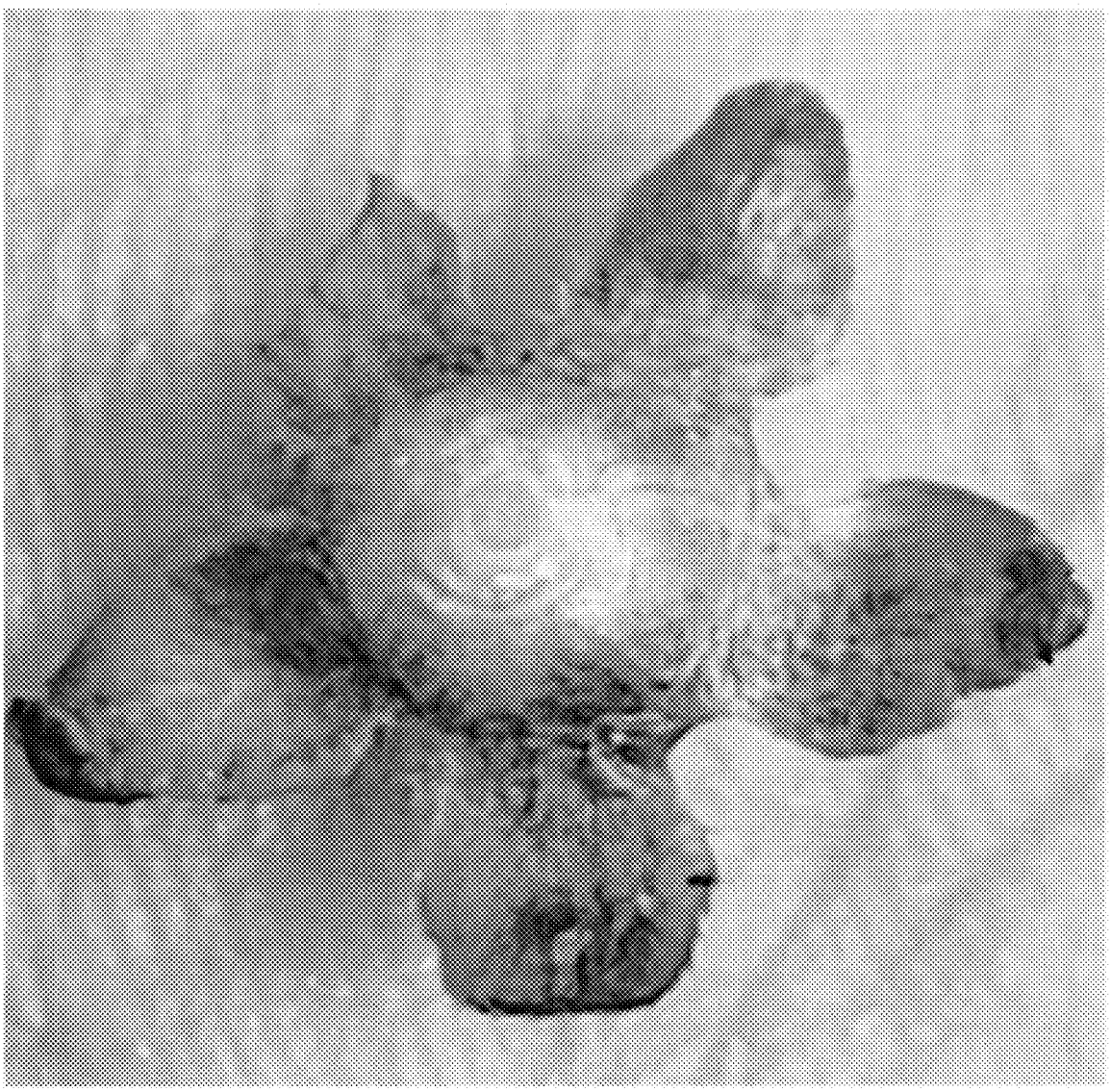

FIG. 1 shows a tree of the claimed variety;
FIG. 2 shows a branch and leaves of the claimed variety;
FIG. 3 shows the upper surface of a leaf of the claimed variety;
FIG. 4 shows the lower surface of a leaf of the claimed variety;
FIG. 5 shows a flower of the claimed variety; and,
FIG. 6 shows the sepals of the claimed variety.

DETAILED BOTANICAL DESCRIPTION OF THE VARIETY

The following detailed botanical description is based on observations made at Yuba City, California during the 2023 growing season of 6-year-old trees grown on their own roots. All colors are described according to the RHS Colour Chart (Royal Horticultural Society, London, 6$^{th}$ edition). It should be understood that the characteristics described will vary somewhat depending upon cultural practices and climatic conditions and will vary with location and season. Quantified measurements are expressed as an average of measurements taken from a number of individual plants of the new variety. The measurements of any individual plant or any group of plants of the new variety may vary from the stated average.

Tree:

*Vigor.*—Reduced; 60% to 65% of standard.
*Habit, shape.*—Wide, vase-shaped.
*Height.*—3.35 m.
*Spread.*—4.5 m.
*Trunk diameter at* 30 *cm above the ground.*—8.5 cm.
*Bark texture.*—Smooth.
*Bark color.*—Greyed-green 197B.
*Lenticel size.*—0.5 cm to 1 cm.
*Lenticel color.*—Grey-brown N199D.
*Lenticel density per cm*$^2$.—0 to 2.

Branch (fruiting branches located at around 1 m above the ground):
*Length.*—60 cm to 90 cm.
*Diameter.*—5.5 to 9.0 cm.
*Crotch angle.*—About 60°.
*Bark color.*—Brown 200 C.
*Bark texture.*—Smooth.
*Lenticel length.*—1 mm to 2 mm.
*Lenticel width.*—<1 mm.
*Lenticel color.*—Grey-brown N199D.
*Lenticel density per cm*$^2$.—0 to 6.

One year old shoot:
*Length.*—44 cm to 120 cm.
*Diameter.*—0.7 cm.
*Pubescence.*—Absent.
*Color.*—Grey-brown 199A.
*Feathering.*—Weak.
*Internode length.*—2.2 cm to 3.0 cm.
*Lenticel length.*—<1 mm.
*Lenticel width.*—<1 mm.
*Lenticel color.*—Greyed-orange 165D.
*Lenticel density per cm*$^2$.—0 to 20.

Flower buds:
*Stage described.*—Dormant.
*Quantity per spur.*—Two.
*Bud shape.*—Conical.
*Apex shape.*—Acute.
*Length.*—4 mm to 6 mm.
*Diameter.*—1.5 mm to 3 mm.
*Color.*—Brown 200B.

Flowers:
*Diameter of fully open flower.*—20 mm to 24 mm.
*Depth of fully open flower.*—15 mm to 19 mm.
*Relative position of petal margin.*—Free.
*Pedicel length.*—1.1 mm to 1.4 mm.
*Pedicel diameter.*—0.9 mm to 1.2 mm.
*Pedicel color.*—Yellow-green 144A.
*Number of flowers per cluster.*—1 to 2.
*Date of first bloom.*—9 Feb. (2023).
*Date of full bloom.*—20 Feb. (2023).
*Pollination requirement.*—Sexually sterile rootstock requires no pollination.

Petals:
*Number per flower.*—5.
*Length.*—15.5 mm to 17.8 mm.
*Width.*—9.6 mm to 10.9 mm.
*Petal shape.*—Obovate.
*Apex shape.*—Rounded.
*Base shape.*—Attenuate.
*Margin.*—Entire.
*Color of upper surface.*—White N155D.
*Color of lower surface.*—White N155D.

Pistil:
*Length.*—10.0 mm to 12.4 mm.
*Color.*—Yellow-green 150C.

Stigma:
*Diameter.*—0.6 mm to 0.7 mm.
*Color.*—Yellow-green 150A.

Style:
*Length.*—8.5 mm to 10.9 mm.
*Color.*—Yellow-green 150C.

Ovary:
*Length.*—0.7 mm to 1.2 mm.
*Color.*—Yellow 11A.

Stamens:
*Quantity.*—33 to 40.
*Anther length.*—1.2 mm to 1.4 mm.
*Anther color.*—Yellow 12A.
*Filament diameter.*—0.3 mm to 0.4 mm.
*Filament color.*—White NN155D.
*Pollen.*—Present in moderate amount.
*Pollen color.*—Greyed-orange 163A.

Sepals:
*Quantity.*—Five.
*Color.*—Yellow-green 144A red 53B.
*Sepal shape.*—Deltoid.
*Apex shape.*—Rounded to obtuse.
*Length.*—3.8 mm to 4.8 mm.
*Margin.*—Serrate and entire.

Leaves:
*Length.*—8.3 cm to 14 cm.
*Width.*—3.5 cm to 5.5 cm.
*Blade margin.*—Serrate.
*Leaf shape.*—Elliptic.
*Apex shape.*—Acuminate.
*Base shape.*—Cuneate.
*Attitude in relation to shoot.*—Outward.
*Color of upper surface.*—Yellow-green 146A.
*Color of lower surface.*—Yellow-green 146C.

Petiole:
*Length.*—9 mm to 12 mm.
*Diameter.*—1 mm to 1.3 mm.
*Color.*—Green 141D.
*Glands.*—Present; diameter 0.8 mm; color yellow 2A; shape circular and reniform.

Fruit: Plant is sterile and forms no fruit.

Chilling requirement: Approximately 480 chill units, far lower than other Myrobalan-plum hybrid rootstocks 'AP 1' and 'PAC 941' (U.S. Plant Pat. No. 21,556, sold as Rootpac®R).

Cold hardiness: Not specifically tested but believed cold hardy; has survived winter in Michigan, U.S.A.

Disease resistance/susceptibility: The rootstock has extremely high tolerance to heavy, wet soils and is less susceptible to root- and crown-rots caused by *Phytophthora* species. 'DA 6' is resistant to root-knot nematodes.

Market use: Vigor-reducing rootstock for almond (*Prunus dulcis*), prune plum (*Prunus domestica*), peach (*Prunus persica*) and apricot (*Prunus armeniaca*).

The invention claimed is:

1. A new and distinct hybrid plum tree named 'DA 6' substantially as illustrated and described herein.

* * * * *